(12) United States Patent
Friedman et al.

(10) Patent No.: US 7,381,189 B2
(45) Date of Patent: Jun. 3, 2008

(54) TEMPERATURE AND RESPIRATION ACQUISITION APPARATUS AND METHOD

(75) Inventors: Bruce Friedman, Tampa, FL (US); Chris Dedyo, Lutz, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 814 days.

(21) Appl. No.: 10/698,229

(22) Filed: Oct. 31, 2003

(65) Prior Publication Data

US 2005/0096558 A1    May 5, 2005

(51) Int. Cl.
*A61B 5/08* (2006.01)
*A61B 5/00* (2006.01)

(52) U.S. Cl. .............. 600/538; 600/529; 600/549; 600/301

(58) Field of Classification Search ........... 600/484, 600/483, 481, 300, 301, 529–543, 549
See application file for complete search history.

(56) References Cited

U.S. PATENT DOCUMENTS

| | | | |
|---|---|---|---|
| 3,884,219 A | 5/1975 | Richardson et al. | |
| 3,999,537 A | 12/1976 | Noiles | |
| 4,036,211 A | 7/1977 | Veth et al. | |
| 4,202,353 A * | 5/1980 | Hirsch et al. | 600/537 |
| 4,222,391 A | 9/1980 | Rawson et al. | |
| 4,777,963 A | 10/1988 | McKenna | |
| 5,161,541 A | 11/1992 | Bowman et al. | |
| 5,311,875 A | 5/1994 | Stasz | |
| 5,518,002 A * | 5/1996 | Wolf et al. | 600/538 |
| 5,558,099 A | 9/1996 | Bowman et al. | |
| 6,733,464 B2 * | 5/2004 | Olbrich et al. | 600/538 |

* cited by examiner

*Primary Examiner*—Charles A. Marmor, II
*Assistant Examiner*—Navin Natnithithadha
(74) *Attorney, Agent, or Firm*—Andrus, Sceales, Starke & Sawall, LLP

(57) ABSTRACT

A device and method for simultaneously acquiring a temperature and a respiration rate of a patient. In some embodiments of the invention, the device can include a probe, a temperature sensing element coupled to the probe, a disposable cover that can be positioned over the probe, and a respiration sensing element coupled to the disposable cover. In other embodiments of the invention, the device can include a probe having a temperature sensing element, a transmitter, and a receiver. The device can further include a probe cover having a respiration sensing element that can be positioned over the probe.

48 Claims, 5 Drawing Sheets

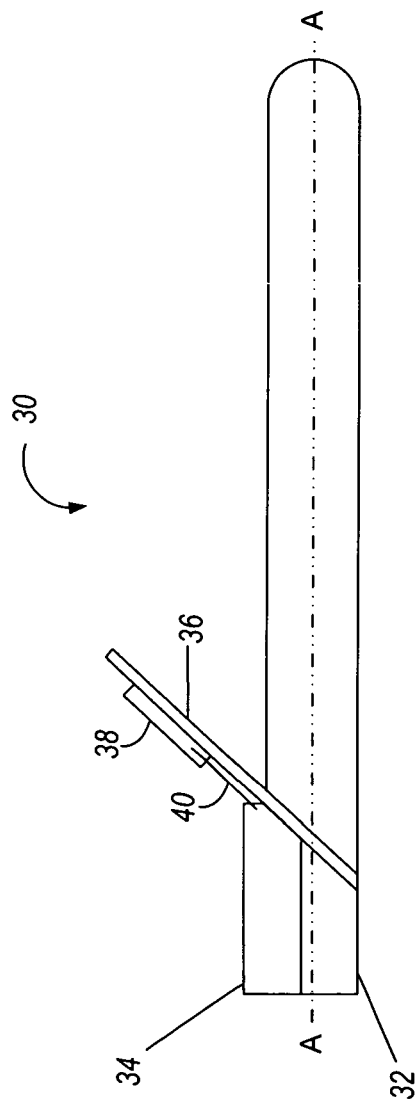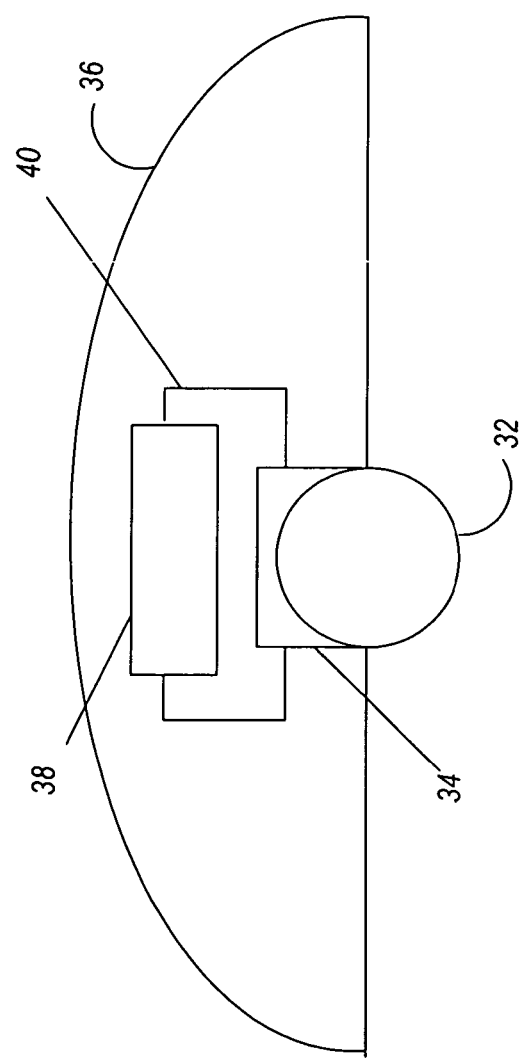

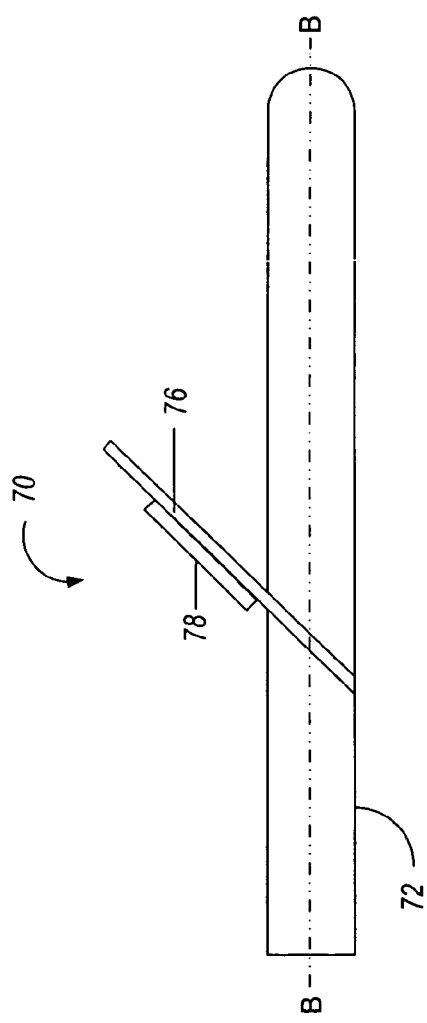
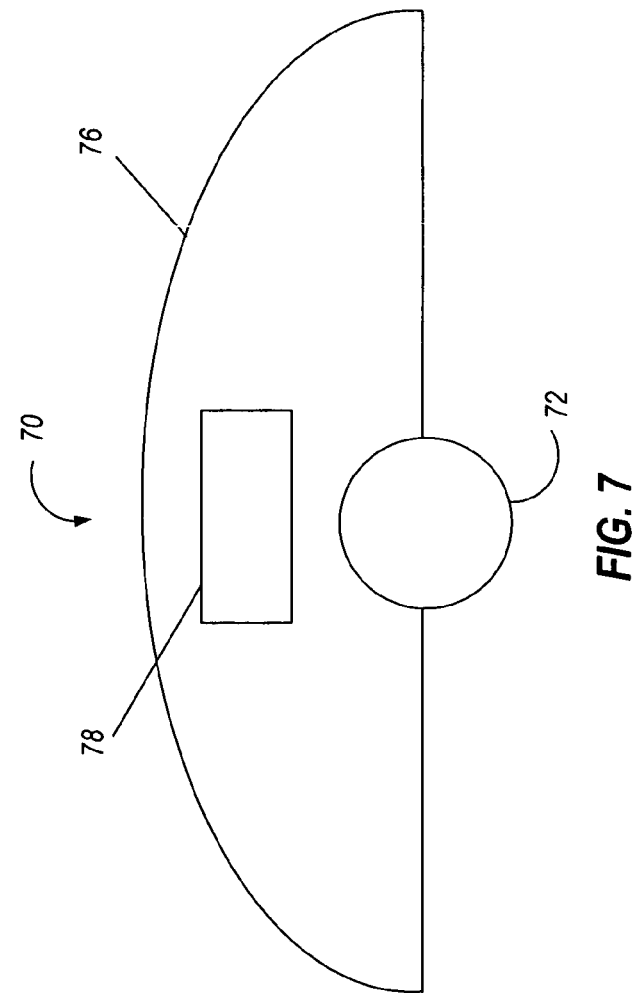

TEMPERATURE AND RESPIRATION ACQUISITION APPARATUS AND METHOD

BACKGROUND OF THE INVENTION

It is accepted clinical practice in acute care areas of the hospital to measure patient vital signs on an infrequent basis, at time intervals ranging from one hour to eight hours. In these parts of the hospital, monitors are moved from patient to patient, and the sensors are attached to the patient only for the duration of the measurement. Current multiparameter monitors for use in acute care hospitals provide automated methods for noninvasively measuring blood pressure, pulse oximetry, pulse rate and temperature.

BRIEF DESCRIPTION OF THE INVENTION

Current instrumentation does not provide a method for electronically measuring respiration rate in acute care patients or patients in other areas of hospitals or clinics unless ECG electrodes have been applied to the patient. ECG is not normally monitored in patients in lower acuity areas of a hospital or clinic.

One embodiment of the invention can include a device for simultaneously acquiring a temperature and a respiration rate of a patient. The device can include a probe, a temperature sensing element coupled to the probe, a disposable cover that can be positioned over the probe, and a respiration sensing element coupled to the disposable cover.

Other embodiments of the invention can include a device a with probe having a temperature sensing element, a transmitter, and a receiver. The device can further include a probe cover having a respiration sensing element that can be positioned over the probe. The transmitter can send a signal toward the respiration sensing element, the respiration sensing element can reflect the signal toward the receiver, and the receiver can generate an output based on the reflected signal representing the respiration rate.

The invention can include a method of simultaneously acquiring a temperature and a respiration rate of a patient. The method can include covering a probe with a disposable cover. In some embodiments, a temperature sensing element can be coupled to the probe, and a respiration sensing element can be coupled to the disposable cover. The method can further include inserting the probe and the disposable cover into the patient's mouth, and simultaneously sensing a temperature of the patient and a respiration rate of the patient.

Other features and advantages of the invention will become apparent to those of ordinary skill in the art upon review of the following description, claims and drawings.

BRIEF DESCRIPTION OF THE DRAWINGS

FIG. 3 is a side elevational view of a respiration sensing portion of the temperature and respiration sensing instrument of FIG. 1.

FIG. 4 is a front elevational view of the respiration sensing portion of FIG. 3 as viewed from the proximal end.

FIG. 6 is a side elevational view of a respiration sensing portion of the temperature and respiration sensing instrument of FIG. 5.

FIG. 7 is a front elevational view of the respiration sensing portion of FIG. 6 as viewed from the proximal end.

DETAILED DESCRIPTION OF THE INVENTION

Figure 1:
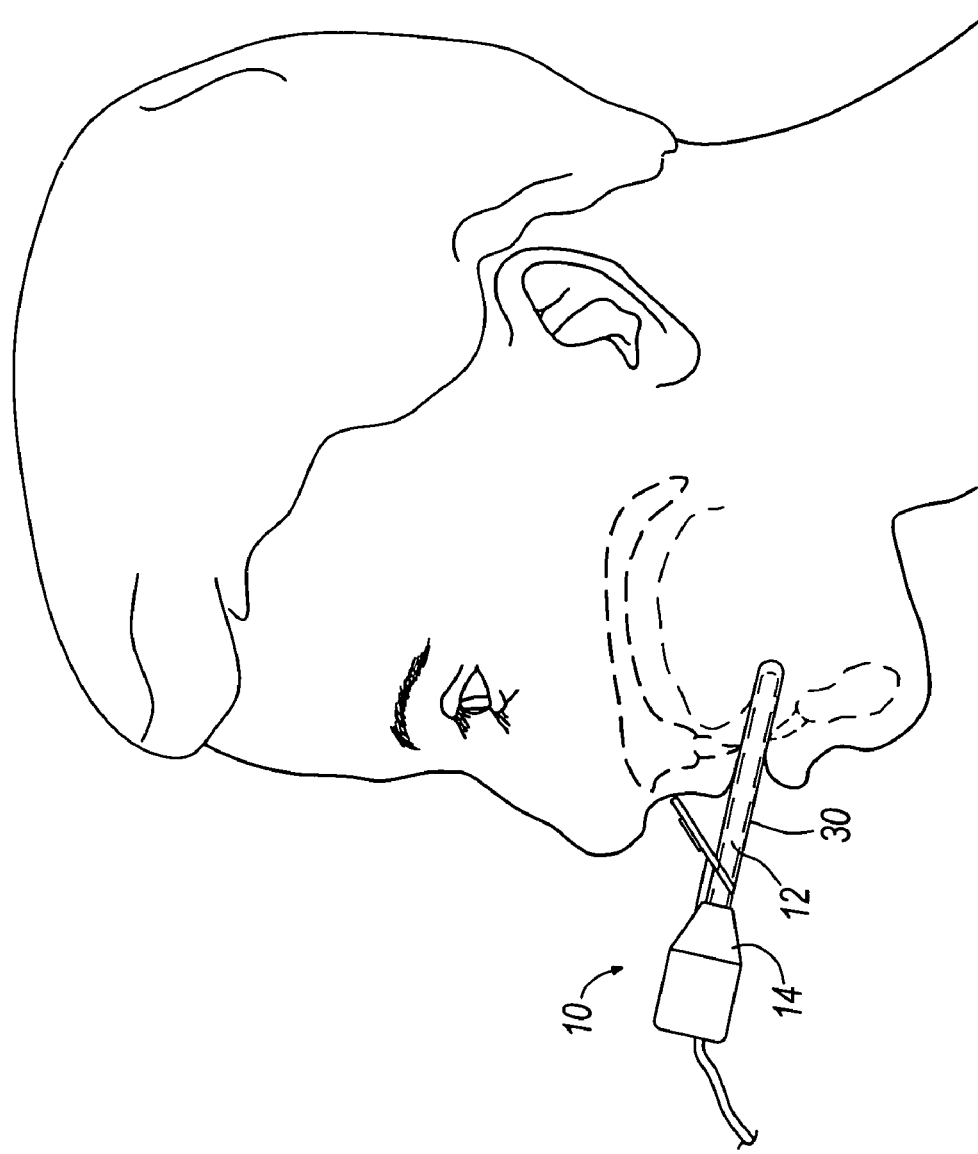
FIG. 1 is a side elevational view of a temperature and respiration sensing instrument according to one embodiment of the invention positioned in a patient's mouth.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings and can include electrical connections or couplings whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be used to implement the invention. Furthermore, and as described in subsequent paragraphs, the specific mechanical configurations illustrated in the drawings are intended to exemplify embodiments of the invention and that other alternative mechanical configurations are possible.

FIGS. 1-4 illustrate a temperature and respiration sensing instrument 10 according to one embodiment of the invention. FIG. 1 illustrates the temperature and respiration sensing instrument 10 positioned sublingually in a patient's mouth (i.e., positioned in any suitable region under a patient's tongue). The temperature and respiration sensing instrument 10 has a distal end positionable within the patient's mouth and a proximal end which protrudes outwardly from the patient's mouth. The terms "proximal" and "distal" are used to describe portions of the temperature and respiration sensing instrument 10 with respect to a caregiver or other healthcare personnel operating the temperature and respiration sensing instrument 10. The proximal end of the temperature and respiration sensing instrument 10 can be further connected to any suitable monitoring and/or recording equipment including, without limitation, DINAMAP® ProCare Monitors, DINAMAP® Pro Series Monitors, and any other monitoring and/or recording equipment capable of being connected to the temperature and respiration sensing instrument 10 for displaying, recording and/or calculating at least one of temperature and respiration rate.

The temperature and respiration sensing instrument 10 can include a probe 12 and a probe cover 30, as shown in FIGS. 1-4. The probe 12 and the probe cover 30 each have a proximal end and a distal end that correspond to the proximal end and the distal end of the entire temperature and respiration sensing instrument 10 described above. As shown in to FIG. 2, the probe 12 can include a collar 14 positioned at the proximal end, a connector 16, a barrel 18, a distal cap 20, and a cable 22. The collar 14 can provide a connector for the cable 22, as well as strain relief for the cable 22. In other words, the collar 14 can allow the cable 22 to extend from the proximal end of the temperature and respiration sensing instrument 10 to monitoring and/or recording equipment without gravity or other forces acting on a portion of the cable 22, thereby maintaining the electrical connection between the temperature and respiration sensing instrument 10 and the monitoring and/or recording equipment. The collar 14 can also provide a handle for a user to hold the probe 12 and manipulate the probe 12 with respect to a patient's mouth. The collar 14 can further provide support for the barrel 18 of the probe 12. The cable 22 can connect the temperature and respiration sensing instrument 10 to any suitable monitoring and/or recording equipment, such as the equipment described above. The connector 16 can be positioned adjacent to the collar 14 and can be connected to the cable 22 through the interior of the collar 14.

Figure 2:
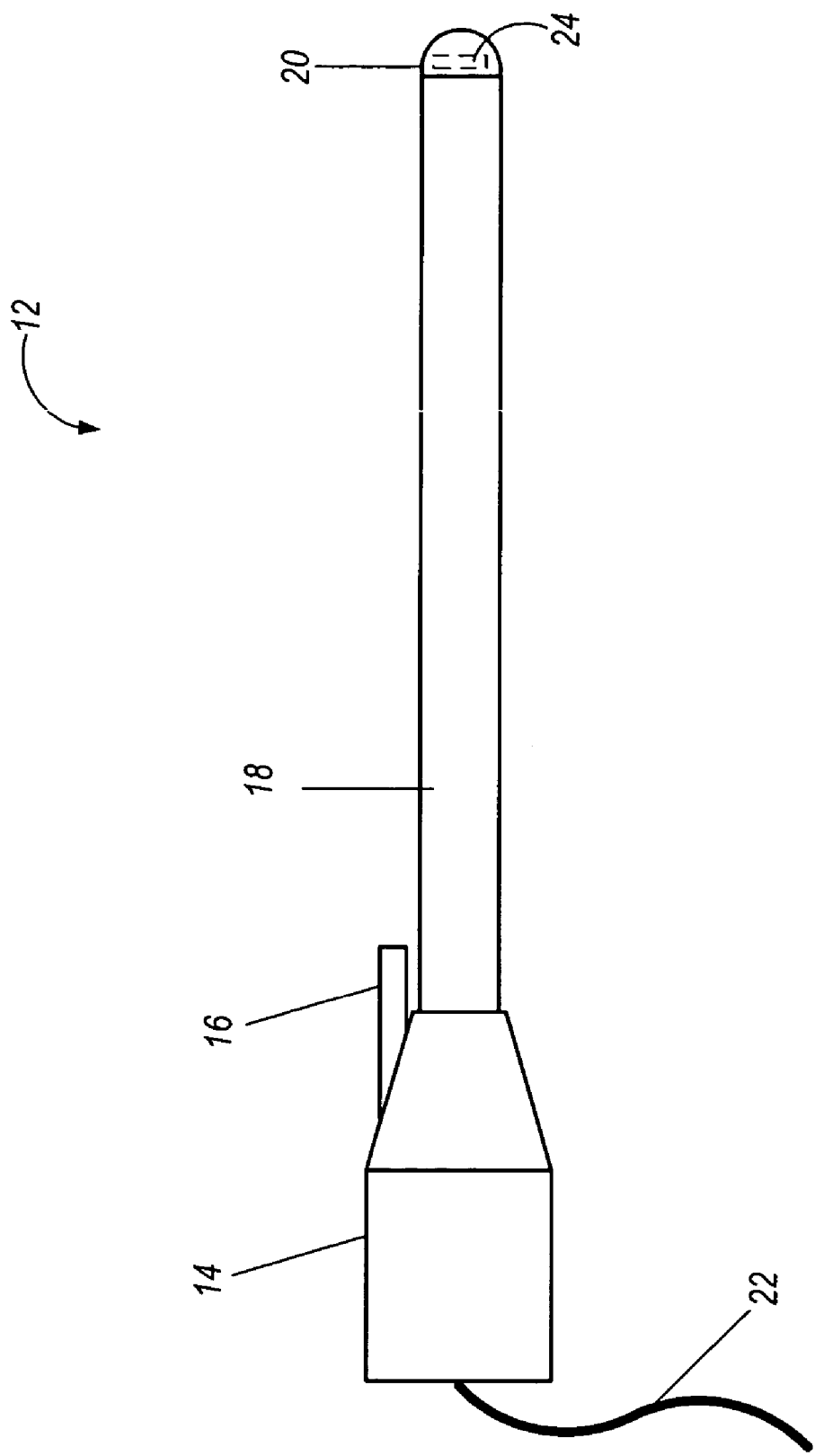
FIG. 2 is a side elevational view of a temperature sensing portion of the temperature and respiration sensing instrument of FIG. 1.

As also shown in FIG. 2, the barrel 18 can include a temperature sensing portion of the temperature and respiration sensing instrument 10. The distal cap 20 is coupled to the distal end of the barrel 18. A temperature sensing element 24 for measuring sublingual temperature can be positioned within the distal cap 20, which can provide a method of securing the temperature sensitive element and can provide thermal contact with the temperature sensitive element. The distal cap 20 can be constructed of any suitable thermally-conductive material, such as a metal, a metal alloy, or a thermally-conductive polymer. The temperature sensing element 24 can be any suitable temperature sensor, including without limitation, a thermistor, a thermocouple, or any other suitable sensor or transducer known to those of ordinary skill in the art capable of generating an output signal indicative of the patient's temperature.

One embodiment of the probe cover 30 is shown in FIGS. 3 and 4. As shown in FIG. 3, the probe cover 30 can include an elongated housing 32, which can be positioned over the barrel 18 of the probe 12 shown in FIG. 2. The probe cover 30 can be constructed of any suitable material (e.g., polyethylene, polypropylene, or other suitable plastics) that is biocompatible and that is thin enough to allow conduction of sublingual temperature changes to the temperature sensing element 24 located within the distal cap 20. A plate 36 (for example, a semi-circular plate) can be coupled to the housing 32. The plate 36 and the housing 32 can be constructed from the same material and can be integrally connected. However, in other embodiments, the housing 32 and the plate 36 can be separate components that are assembled together. The plate 36, as shown in FIG. 1, can be shaped in any suitable manner to rest on the patient's lip and beneath the patient's nose when the temperature and respiration sensing instrument 10 is inserted into the patient's mouth. As shown in FIG. 3, the plate 36 can be positioned at an angle of less than ninety degrees with respect to a longitudinal axis A-A of the probe cover 30.

FIG. 4 illustrates one embodiment of the probe cover 30 from its proximal end. A respiration transducer or respiration sensing element 38 can be coupled to the plate 36 such that the respiration sensing element 38 can sense nasal respiration when the temperature and respiration sensing instrument 10 is positioned in a patient's mouth and can generate an output signal indicative of the patient's respiration rate. A connector 34 can be coupled to the housing 32 and connected to the respiration sensing element 38 via wires 40, as shown in FIG. 4. The connector 34 can connect mechanically with the connector 16 of the probe 12, so that the respiration sensing element 38 can be electrically connected to the cable 22 and any suitable monitoring and/or recording equipment. In some embodiments, the connector 16 is a male member that can be received by the connector 34 that includes a female recess.

The respiration sensing element 38 in some embodiments of the invention can also include a temperature sensitive element. For example, the respiration sensing element 38 can include a thermistor that measures respiration rate by measuring the change in resistance as exhaled air moves over the respiration sensing element 38. The monitoring and/or recording equipment connected to the temperature and respiration sensing instrument 10 can provide power to the respiration sensing element 38 (whether or not the respiration sensing element 38 also senses temperature). The temperature and respiration sensing instrument 10 can generate and transmit one or more signals representing the sensed temperature and/or the respiration rate to the monitoring and/or recording equipment. In some embodiments, the monitoring and/or recording equipment can also sense a change in resistance as air moves over the sensing element in order to measure respiration rate. A thermistor, for example, includes a thermally-sensitive resistor in which resistance decreases [i.e., a negative temperature coefficient (NTC) thermistor] or increases [i.e., a positive temperature coefficient (PTC) thermistor] as the actual temperature increases. As exhaled air having a temperature greater than ambient air passes over the thermistor, the resistance of the thermistor can increase or decrease by a predictable amount, and the resistance measured over time can illustrate the periods of time in which the patient was exhaling From the resistance versus time data, the respiration rate can be calculated.

The respiration sensing element 38 can also have temperature sensing capabilities by including a thermocouple, temperature-sensitive liquid crystals, and/or any other suitable temperature sensor or transducer known to those of ordinary skill in the art. For example, in some embodiments, the respiration sensing element 38 can include a thermocouple, which can be constructed as fused junctions of two materials (e.g., copper and constantan). When the thermocouple is heated, a current can flow from a measuring side (i.e., a hot junction) to a reference side (i.e., a cold junction). An electric potential can develop between the measuring side and the reference side, which can be measured in volts. Therefore, respiration rate can be calculated from voltage versus time data.

Figure 5:
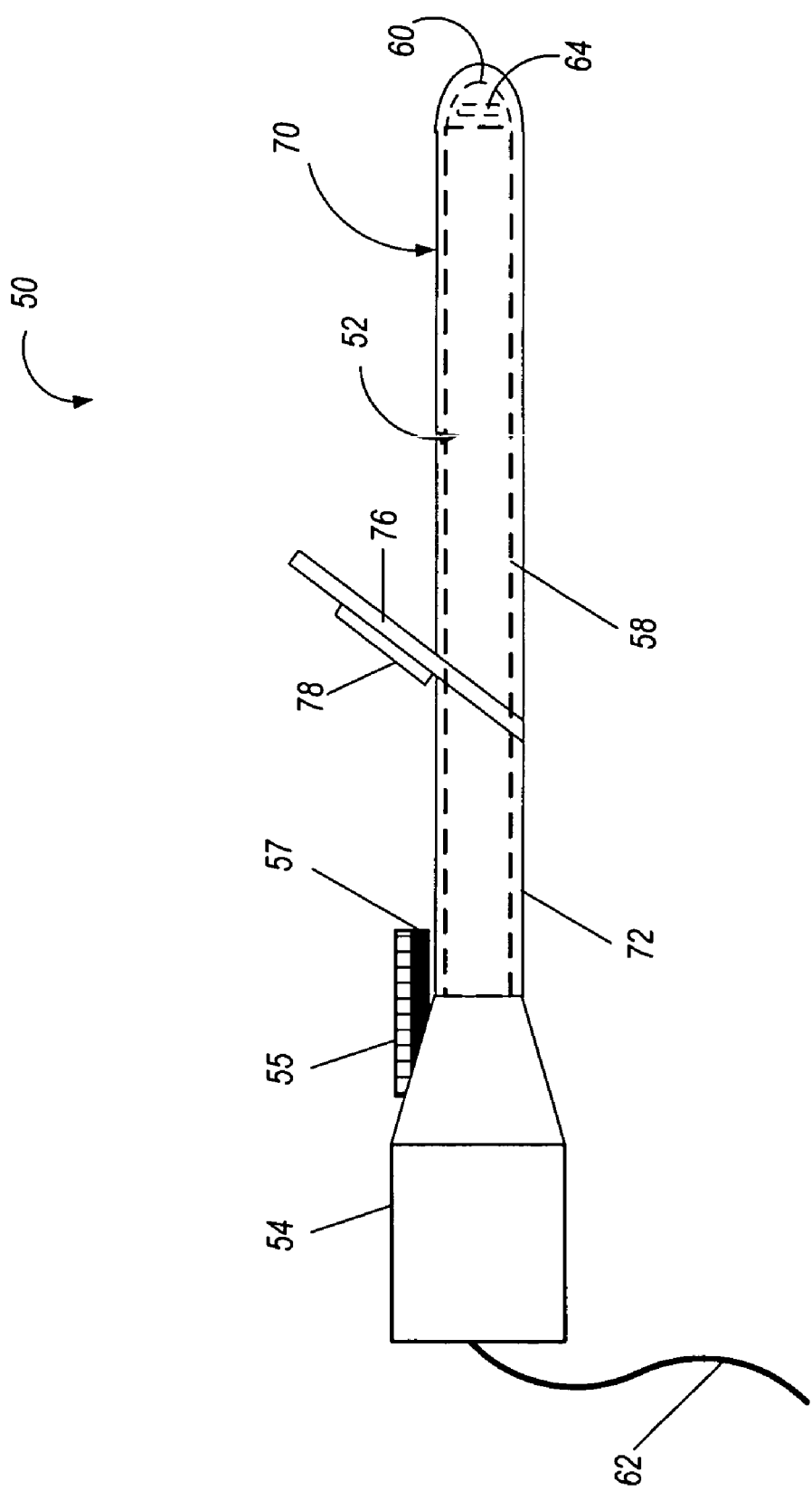
FIG. 5 is a side elevational view of a temperature and respiration sensing instrument according to another embodiment of the invention.

In other embodiments, the respiration sensing element 38 can include temperature-sensitive liquid crystals made of chemical compounds having the property of reflecting light when having a temperature in a range of 26 to 40° C., for example, and changing the color of the reflected light based on temperature. The liquid crystals can be formulated to change color in response to temperatures near, above and below human body temperature (i.e., 37° C.). However, the liquid crystals can operate in any suitable range or subrange for sensing human body temperatures. As exhaled air passes over the liquid crystals, the liquid crystals can change color in response to the temperature change. The color change over time can indicate respiration rate. FIGS. 5-7 illustrate a temperature and respiration sensing element of the invention capable of sensing a color change in the respiration sensing element, as explained below. In general, one or more suitable sensing elements can be coupled to the plate 36 in order to sense respiration rate by sensing a change in temperature of the air surrounding the respiration sensing element 38 as exhaled air periodically passes over the respiration sensing element 38.

FIGS. 5-7 illustrate another embodiment of the invention. FIG. 5 illustrates an assembled temperature and respiration sensing instrument 50 including a probe 52 and a probe cover 70. The probe 52 can include a collar 54, a barrel 58, a distal cap 60 that houses a temperature sensing element 64, and a cable 62. For example, a transmitter and a receiver can be coupled to the instrument so that one or more light-emitting diodes (LEDs) 55 and one or more positive-intrinsic-negative (PIN) photodiodes 57 can be positioned adjacent to the collar 54 and connected to the cable 62 and to any suitable monitoring and/or recording equipment. Rather than a mechanical coupling and/or a direct electrical coupling, the LEDs 55 and photodiodes 57 can wirelessly communicate with a respiration sensing element 78 on the probe cover 70.

As shown in FIGS. 5-7, the probe cover 70 can include a housing 72 and a plate 76. As shown in FIG. 6, the plate 76 can be positioned at an angle of less than ninety degrees with respect to a longitudinal axis B-B of the probe cover 70. The plate 76 can be positioned to rest on a patient's lip, beneath the patient's nose, and in line with nasal respiration when the temperature and respiration sensing instrument 50 is positioned sublingually in a patient's mouth. The housing 72 can be shaped to fit over the barrel 58 of the probe 52, as shown in FIG. 5. A respiration sensing element 78 can be coupled to the plate 76.

FIG. 7 illustrates the probe cover 70 from the proximal end with the respiration sensing element 78 coupled to the plate 76. In some embodiments, the respiration sensing element 78 can sense and change color in response to certain components of exhaled air. For example, the sensing element 78 can be sensitive to carbon dioxide ($CO_2$). The respiration sensing element 78 can include a $CO_2$-sensitive dye, which changes color in response to changes in $CO_2$ levels. Alternatively, or in addition, the respiration sensing element 78 can include a moisture sensitive element, which can respond to changes in moisture content between inhaled and exhaled air.

Referring to FIG. 5, light emitted from the LEDs 55 can be reflected off of the respiration sensing element 78. The reflected light and/or a change in reflected light can be measured by the PIN photodiodes 57. A PIN photodiode 57 for use with the temperature and respiration sensing instrument 50 can include a large, neutrally doped intrinsic region positioned between p-doped and n-doped semiconducting regions and can be formulated to exhibit a change in electrical conductivity as a function of intensity, wavelength and modulation rate of incident radiation (i.e., the light emitted from the LEDs 55). The LEDs 55 can emit light toward the respiration sensing element 78 (which is changing over time depending on respiration). The light reflected back to the PIN photodiodes 57 from the respiration sensing element 78 can depend on the color of the respiration sensing element 78. The PIN photodiodes 57 can thus convert the optical power of the reflected light into electrical power. The change in electrical conductivity of the PIN photodiodes 57 can be measured over time, and this data can be used to calculate respiration rate. Other types of respiration sensing elements that change color in response to temperature or a particular component of exhaled air are possible (e.g., temperature-sensitive liquid crystals, as explained above) and are included in the scope of the invention.

In some embodiments, the LEDs 55 can include one red LED and one infrared LED. The LED wavelength of the light emitted by the LEDs can be determined by the requirements of the respiration sensing element 78. Any suitable wavelength or combination of wavelengths can be used without departing from the spirit and scope of the invention. The PIN photodiodes 57 can be broadband photodiodes for use with a wide variety of wavelengths. That is, the PIN photodiodes 57 can be formulated to support a wide range of frequencies, such as from audio to video frequencies. The PIN photodiodes 57 can be formulated to support a wide range of frequencies by dividing the total capacity of the medium into multiple, independent bandwidth channels, where each channel can operate only in a specific range of frequencies.

The probe covers 30 and 70 described above with respect to FIGS. 3 and 6 can be disposable so that cross-contamination between patients can be prevented. The probe cover housings 32 and 72 can be disposable and can be shaped to cover the barrels 18 and 58 of the probes 12 and 52 and the distal caps 20 and 60. As a result, the probe covers 30 and 70 can provide a barrier between the patient's mouth and the temperature sensing elements. In addition, the respiration sensing elements 38 and 78 can be coupled to the plates 36 and 76 so that the respiration sensing elements 38 and 78 can be disposed of with the probe covers 30 and 70, thereby providing single-patient-use respiration transducers 38 and 78. In this manner, some embodiments of the invention can provide a temperature and respiration sensing instrument that substantially prevents cross-contamination between patients while electronically monitoring and/or recording temperature and respiration rate.

In some embodiments, the temperature and respiration sensing instruments 10 and 50 can measure nasal respiration rate. When the elongated housings 32 and 72 (and barrels 18 and 58) are positioned sublingually in a patient's mouth, the patient's mouth can be closed around the housings 32 and 72 so that the patient must breathe primarily through his/her nose. The respiration sensing elements 38 and 78 being coupled to the plates 36 and 76 can result in the respiration sensing elements 38 and 78 being properly positioned for measuring nasal respiration rate.

The respiration sensing elements 38 and 78 being coupled to the disposable probe covers 30 and 70 can result in the respiration sensing elements 38 and 78 being movable relative to the temperature sensing elements 24 and 64 located within the distal caps 20 and 60. Accordingly, the respiration sensing elements 38 and 78 and the temperature sensing elements 24 and 64 may not be fixed with respect to one another so that each can be independently positioned to measure temperature and respiration rate simultaneously.

When the temperature and respiration sensing instruments 10 and 50 are in use, the temperature sensing elements 24 and 64 and the respiration sensing elements 38 and 78 can be constantly sensing, acquiring and/or measuring the patient's temperature and respiration rate. However, the monitoring and/or recording equipment used may only be sampling at a certain rate and may only be sampling, saving, monitoring and/or recording one of the temperature and the respiration rate at a given time. Accordingly, the temperature and respiration sensing instruments 10 and 50 can be used to monitor and/or record temperature and respiration rate simultaneously, but the temperature and respiration sensing instruments 10 and 50 can also be used to monitor and/or record only one of temperature and respiration rate at any given time, even though the temperature sensing elements 24 and 64 and the respiration sensing elements 38 and 78 can be constantly sensing temperature and respiration rate, respectively.

Various features and advantages of the invention are set forth in the following claims.

The invention claimed is:

1. A device for simultaneously acquiring a temperature and a respiration rate of a patient, the device comprising:
   a probe;
   a temperature sensing element coupled to the probe;
   a disposable cover that can be positioned over and moved relative to the probe; and
   a respiration sensing element separate from the temperature sensing element and positioned on the disposable cover such that the respiration sensing element is movable relative to the temperature sensing element and is removable from the probe along with the disposable cover.

2. The device of claim 1 wherein the disposable cover includes a plate, and wherein the respiration sensing element is coupled to the plate.

3. The device of claim 2 wherein the plate is positioned at an angle of less than ninety degrees with respect to a longitudinal axis of the disposable cover so that the plate can rest on the patient's upper lip beneath the patient's nose.

4. The device of claim 1 wherein the probe includes a proximal end and a distal end, and wherein the temperature sensing element is positioned at the distal end in order to sense the patient's sublingual temperature when the probe is inserted into the patient's mouth.

5. The device of claim 1 wherein the probe includes a proximal end and a distal end, and wherein a collar is positioned at the proximal end.

6. The device of claim 1 wherein the probe includes a first connector and the disposable cover includes a second connector that can be connected to the first connector when the disposable cover is positioned over the probe.

7. The device of claim 6 wherein at least one of patient monitoring equipment and data recording equipment provides power to the temperature sensing element and to the respiration sensing element via the connection between the first and second connectors.

8. The device of claim 6 wherein the temperature sensing element and the respiration sensing element provide at least one signal representing a sensed temperature and a sensed respiration rate to at least one of patient monitoring equipment and data recording equipment via the connection between the first and second connectors.

9. The device of claim 1 wherein the temperature sensing element includes a thermistor.

10. The device of claim 1 wherein the temperature sensing element includes a thermocouple.

11. The device of claim 1 wherein the respiration sensing element is positioned on the disposable cover to sense primarily nasal respiration when the patient's mouth is closed over the disposable cover.

12. The device of claim 1 wherein the disposable cover is constructed of at least one of a polyethylene and a polypropylene.

13. The device of claim 1 wherein the probe is constructed of at least one of a metal, a metal alloy, and a thermally-conductive polymer.

14. A device for simultaneously acquiring a temperature and a respiration rate of a patient, the device comprising:
   a probe;
   a temperature sensing element coupled to the probe;
   a disposable cover that can be positioned over the probe; and
   a respiration sensing element coupled to the disposable cover,
   wherein the probe includes at least one light-emitting diode and at least one photodiode,
   the light-emitting diode emitting light toward the respiration sensing element,
   the respiration sensing element reflecting the emitted light,
   the at least one photodiode receiving the reflected light, and
   the photodiode generating a signal representing the respiration rate based on the received light.

15. The device of claim 14 wherein the respiration sensing element reflects the light emitted by the light-emitting diode in response to a change in temperature as the patient inhales and exhales.

16. The device of claim 14 wherein:
   the respiration sensing element is sensitive to a component of exhaled air,
   the respiration sensing element changing color upon sensing the component of exhaled air, and
   the photodiode sensing the change in color and generating a signal representing the presence of the component of exhaled air.

17. The device of claim 16 wherein the respiration sensing element includes a carbon dioxide sensitive dye.

18. The device of claim 16 wherein the respiration sensing element is sensitive to moisture.

19. A device for simultaneously acquiring a temperature and a respiration rate of a patient, the device comprising:
   a probe including a temperature sensing element, a transmitter, and a receiver; and
   a probe cover that can be positioned over the probe, the probe cover including a respiration sensing element,
   the transmitter sending a signal toward the respiration sensing element,
   the respiration sensing element reflecting the signal toward the receiver, and
   the receiver generating an output representing the respiration rate based on the reflected signal.

20. The device of claim 19 wherein the transmitter is at least one light-emitting diode and the receiver is at least one photodiode.

21. The device of claim 19 wherein the respiration sensing element reflects the signal sent by the transmitter in response to a change in temperature as the patient inhales and exhales.

22. The device of claim 19 wherein:
   the respiration sensing element is sensitive to a component of exhaled air,
   the respiration sensing element changing color upon sensing the component of exhaled air; and
   the receiver sensing the change in color and generating an output representing the presence of the component of exhaled air.

23. The device of claim 22 wherein the respiration sensing element includes a carbon dioxide sensitive dye.

24. The device of claim 22 wherein the respiration sensing element is sensitive to moisture.

25. The device of claim 19 wherein the probe cover includes a plate, and wherein the respiration sensing element is coupled to the plate.

26. The device of claim 25 wherein the plate is positioned at an angle of less than ninety degrees with respect to a longitudinal axis of the probe cover so that the plate can rest on the patient's upper lip beneath the patient's nose.

27. The device of claim 19 wherein the probe includes a proximal end and a distal end, and wherein the temperature sensing element is positioned at the distal end in order to sense the patient's sublingual temperature when the probe is inserted into the patient's mouth.

28. The device of claim 19 wherein the probe includes a proximal end and a distal end, and wherein a collar is positioned at the proximal end.

29. The device of claim 19 wherein the probe includes a first connector and the probe cover includes a second connector that can be connected to the first connector when the probe cover is positioned over the probe.

30. The device of claim 29 wherein at least one of patient monitoring equipment and data recording equipment provides power to the temperature sensing element and to the respiration sensing element via the connection between the first and second connectors.

31. The device of claim 29 wherein the temperature sensing element and the respiration sensing element provide at least one signal representing a sensed temperature and a sensed respiration rate to at least one of patient monitoring equipment and data recording equipment via the connection between the first and second connectors.

32. The device of claim 19 wherein the temperature sensing element includes a thermistor.

33. The device of claim 19 wherein the temperature sensing element includes a thermocouple.

34. The device of claim 19 wherein the respiration sensing element is a separate element from the temperature sensing element so that the respiration sensing element can be moved independently of the temperature sensing element with respect to at least one of the patient's nose and mouth.

35. The device of claim 19 wherein the respiration sensing element is positioned on the probe cover in order to sense primarily nasal respiration when the patient's mouth is closed over the probe cover.

36. The device of claim 19 wherein the probe cover is constructed of at least one of a polyethylene and a polypropylene.

37. The device of claim 19 wherein the probe is constructed of at least one of a metal, a metal alloy, and a thermally-conductive polymer.

38. A method of simultaneously acquiring a temperature and a respiration rate of a patient, the method comprising:
covering a probe with a disposable cover, a temperature sensing element being coupled to the probe, a respiration sensing element being positioned on the disposable cover;
inserting the probe and the disposable cover into the patient's mouth;
moving the probe cover and the attached respiration sensing element independently of the probe and the temperature sensing element to position the respiration sensing element in a desired location relative to at least one of the patient's nose and mouth;
simultaneously sensing a temperature of the patient and a respiration rate of the patient;
removing the probe and the disposable cover from the patient's mouth;
removing the disposable cover and the attached respiration sensing element from the probe; and
disposing of the disposable cover and the respiration sensing element to prevent cross-contamination between patients.

39. The method of claim 38 wherein the disposable cover includes a plate positioned at an angle of less than ninety degrees with respect to a longitudinal axis of the disposable cover, and further comprising resting the plate on the patient's upper lip beneath the patient's nose.

40. The method of claim 38 and further comprising sensing a sublingual temperature of the patient when the probe is inserted into the patient's mouth.

41. The method of claim 38 and further comprising attaching a first connector on the probe to a second connector on the disposable cover in order to mechanically couple the disposable cover to the probe and to electrically connect the respiration sensing element to the probe.

42. The method of claim 41 and further comprising providing power from at least one of patient monitoring equipment and data recording equipment to the temperature sensing element and to the respiration sensing element via the connection between the first and second connectors.

43. The method of claim 41 and further comprising generating at least one signal representing a sensed temperature and a sensed respiration rate.

44. The method of claim 43 and further comprising providing the at least one signal to at least one of patient monitoring equipment and data recording equipment via the connection between the first and second connectors.

45. The method of claim 38 and further comprising sensing primarily nasal respiration when the patient's mouth is closed over the disposable cover.

46. A method of simultaneously acquiring a temperature and a respiration rate of a patient, the method comprising:
covering a probe with a disposable cover, a temperature sensing element being coupled to the probe, a respiration sensing element being coupled to the disposable cover;
inserting the probe and the disposable cover into the patient's mouth;
sending light from at least one light-emitting diode coupled to the probe toward the respiration sensing element, the respiration sensing element reflecting the light sent by the light-emitting diode;
receiving the reflected light with at least one photodiode;
generating a signal representing a respiration rate of the patient based on the light received by the at least one photodiode; and
simultaneously sensing the temperature of the patient and the respiration rate of the patient.

47. The method of claim 46 and further comprising sensing a change in temperature when the patient inhales and exhales, and reflecting the light sent by the light-emitting diode in response to the change in temperature.

48. The method of claim 46 and further comprising:
sensing a component of exhaled air with the respiration sensing element;
changing a color of the respiration sensing element in response to the sensed component of exhaled air;
sensing the change in color with the at least one photodiode; and
generating a signal representing the presence of the component of exhaled air based on the sensed change in color.

* * * * *